(12) United States Patent
Sugiyama et al.

(10) Patent No.: US 11,596,583 B2
(45) Date of Patent: Mar. 7, 2023

(54) RAW MATERIAL FOR COSMETIC AND OIL-IN-WATER EMULSION COSMETIC COMPRISING CORE-CORONA POLYMER PARTICLE

(71) Applicant: Shiseido Company, Ltd., Tokyo (JP)

(72) Inventors: Yuki Sugiyama, Kanagawa (JP); Ryushi Fukuhara, Kanagawa (JP)

(73) Assignee: Shiseido Company, Ltd., Tokyo (JP)

( * ) Notice: Subject to any disclaimer, the term of this patent is extended or adjusted under 35 U.S.C. 154(b) by 200 days.

(21) Appl. No.: 16/982,348

(22) PCT Filed: Mar. 22, 2019

(86) PCT No.: PCT/JP2019/012146
§ 371 (c)(1),
(2) Date: Sep. 18, 2020

(87) PCT Pub. No.: WO2019/182127
PCT Pub. Date: Sep. 26, 2019

(65) Prior Publication Data
US 2021/0007945 A1    Jan. 14, 2021

(30) Foreign Application Priority Data

Mar. 23, 2018  (JP) .............................. JP2018-057243

(51) Int. Cl.
| | |
|---|---|
| *A61K 8/02* | (2006.01) |
| *A61K 8/06* | (2006.01) |
| *A61K 8/85* | (2006.01) |
| *A61Q 19/00* | (2006.01) |

(52) U.S. Cl.
CPC .............. *A61K 8/0241* (2013.01); *A61K 8/06* (2013.01); *A61K 8/85* (2013.01); *A61Q 19/00* (2013.01)

(58) Field of Classification Search
None
See application file for complete search history.

(56) References Cited

U.S. PATENT DOCUMENTS

| | | |
|---|---|---|
| 6,440,399 B1 | 8/2002 | Gers-Barlag et al. |
| 2005/0049380 A1 | 3/2005 | Iyanagi |
| 2012/0172457 A1 | 7/2012 | Braun et al. |

(Continued)

FOREIGN PATENT DOCUMENTS

| | | |
|---|---|---|
| JP | 01-284516 A | 11/1989 |
| JP | 10-268576 A | 10/1998 |

(Continued)

OTHER PUBLICATIONS

Kaneda et al., "Swelling behavior of PMMA-g-PEO microgel particles by organic solvents," Journal of Colloid and Interface Science, 2004, 274:49-54.

*Primary Examiner* — Dominic Lazaro
(74) *Attorney, Agent, or Firm* — Foley & Lardner LLP

(57) ABSTRACT

Provided are: a core-corona polymer particle excellent in emulsion stability and feeling of use, and a raw material for a cosmetic and an oil-in-water emulsion cosmetic comprising the particle. Certain embodiments of the present invention provides a core-corona polymer particle obtained by radical-polymerizing a polyethylene oxide macromonomer represented by formula (1) and one or two or more of hydrophobic monomers represented by formulas (2) and (3) under conditions (A) to (D).

5 Claims, 1 Drawing Sheet

(56) References Cited

U.S. PATENT DOCUMENTS

| | | | |
|---|---|---|---|
| 2014/0341957 A1 | 11/2014 | Yang et al. | |
| 2014/0343170 A1 | 11/2014 | Sugiyama et al. | |
| 2016/0001244 A1* | 1/2016 | Sugiyama | C08L 33/12 512/1 |
| 2017/0239165 A1 | 8/2017 | Sugiyama et al. | |
| 2019/0290572 A1 | 9/2019 | Sugiyama et al. | |

FOREIGN PATENT DOCUMENTS

| | | |
|---|---|---|
| JP | 2001-518111 A | 10/2001 |
| JP | 2002-322219 A | 11/2002 |
| JP | 2003-055164 A | 2/2003 |
| JP | 2005-015623 A | 1/2005 |
| JP | 2005-213448 A | 8/2005 |
| JP | 2005-213485 A | 8/2005 |
| JP | 2006-161026 A | 6/2006 |
| JP | 4426859 B2 | 3/2010 |
| JP | 2012-241004 A | 12/2012 |
| JP | 2014-534275 A | 12/2014 |
| JP | 2015-091964 A | 5/2015 |
| JP | 6403854 B2 | 9/2018 |
| WO | WO-2006/051746 A1 | 5/2006 |
| WO | WO-2011/048757 A1 | 4/2011 |
| WO | WO-2013/094298 A1 | 6/2013 |
| WO | WO-2016/021338 A1 | 2/2016 |
| WO | WO-2019/182124 A1 | 9/2019 |
| WO | WO-2019/182125 A1 | 9/2019 |
| WO | WO-2019/182126 A1 | 9/2019 |

* cited by examiner

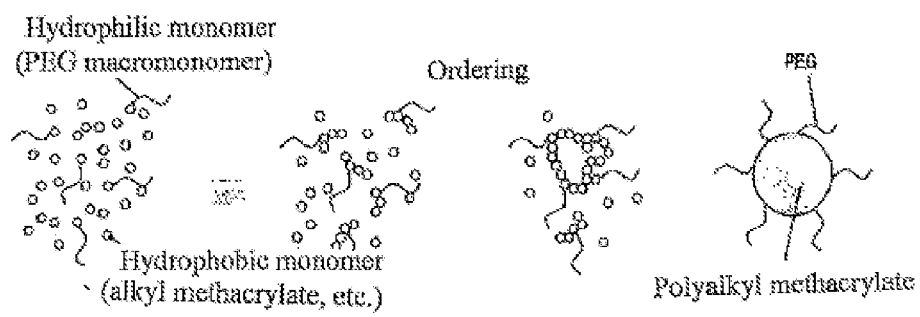

RAW MATERIAL FOR COSMETIC AND OIL-IN-WATER EMULSION COSMETIC COMPRISING CORE-CORONA POLYMER PARTICLE

RELATED APPLICATION

The present application is the U.S. National Stage of PCT/JP2019/012146, filed Mar. 22, 2019, which claims the priority of Japanese Patent Application No. 2018-057243 filed on Mar. 23, 2018, which is incorporated herein.

FIELD OF THE INVENTION

The present invention relates to a raw material for a cosmetic containing a core-corona polymer particle and an oil-in-water emulsion cosmetic containing the same. Particularly, the present invention relates to improvement in the emulsion stability and usability of a cosmetic.

BACKGROUND OF THE INVENTION

For stably dispersing a liquid in another liquid, emulsion cosmetics in the conventional sense require adding a surface-active substance (emulsifier). The emulsifier has an amphiphilic molecular structure and is constituted by polar (hydrophilic) and nonpolar (hydrophobic) moieties.

In emulsion cosmetics for use in cosmetic products, etc., aqueous components and oil components are stably mixed by the emulsifying effect of an added surfactant. Oil-in-water cosmetics are reportedly excellent in feeling of use that confers watery texture because dispersed microdroplets of the oil phase are surrounded by emulsifier shells and the external phase is a continuous water phase. Also, water-in-oil emulsion cosmetics have good spreadability upon application and an excellent water-resistant effect of a makeup film after application because microdroplets of the water phase are dispersed in a continuous oil phase.

Meanwhile, as an increasing number of consumers have placed more emphasis on safety in recent years, some hypersensitive users have a growing demand for oil-in-water emulsion cosmetics or water-in-oil emulsion cosmetics free from even a surfactant that might give irritancy to the skin on rare occasions or containing the surfactant at a content without giving such irritation.

Surfactants have the property of forming a high-order associate with poor feeling of use in association with the elevation of a relative concentration with respect to water or an oil. Therefore, emulsion cosmetics using a surfactant as an emulsifier may impair refreshing feeling and cause stickiness or sliminess due to the elevation of the surfactant concentration of a makeup film in association with solvent volatilization upon application.

A Pickering emulsion method which involves adsorbing a powder onto the interface between an oil phase and a water phase for emulsification is known as a method for producing an oil-in-water emulsion cosmetic without the use of a surfactant. However, an inorganic powder such as a metal oxide or a mineral (e.g., silica) is generally used as the powder for use in the method. However, these powders need to be blended in a large amount due to their weak emulsifying ability. Therefore, the resulting cosmetics disadvantageously offer powderiness or squeaky feeling. Furthermore, oil droplets emulsified with an inorganic powder disadvantageously have low stability because these oil droplets are vulnerable to impact and are easily unified by stirring or shaking (Patent Literature 1).

It is also known that a core-corona microgel (which corresponds to the core-corona polymer particle according to the present invention) obtained by radical-polymerizing a specific polyethylene oxide macromonomer, a specific acrylate derivative monomer, and a specific cross-linkable monomer under specific conditions is very highly swellable in an organic solvent and can be stably emulsified in various types of oils. It has further been reported that an oil-in-water emulsion cosmetic having excellent emulsion stability, less sticky feeling, and less powderiness or squeaky feeling is obtained by using the microgel as an emulsifier. However, a low cross-linking density of the core moiety causes the core structure to collapse upon swelling, whereas too high a cross-linking density causes microgel particles to aggregate. In both the cases, unfortunately, the microgel no longer functions as an emulsifier (Patent Literature 2).

Under these circumstances, there is a demand for the development of a raw material for a cosmetic, comprising a core-corona microparticle excellent in emulsion stability with emulsifying power not influenced by a cross-linking level, and an oil-in-water emulsion cosmetic emulsified with the raw material for a cosmetic.

CITATION LIST

Patent Literature

[Patent Literature 1] Japanese Unexamined Patent Application No. 2001-518111
[Patent Literature 2] Japanese Unexamined Patent Application No. 2006-161026

DISCLOSURE OF THE INVENTION

Problem to be Solved by the Invention

Accordingly, the present invention has been made in light of the conventional techniques. An object of the present invention is to provide a raw material for a cosmetic, comprising a core-corona polymer particle that can be generally used in an oil-in-water emulsion cosmetic, and to provide an oil-in-water emulsion cosmetic emulsified with the microparticle having excellent emulsion stability, less sticky feeling, and less powderiness or squeaky feeling.

Means to Solve the Problem

The present inventors have conducted diligent studies to attain the objects mentioned above and consequently found that a core-corona polymer particle that can be generally used in an oil-in-water emulsion cosmetic is obtained by radical-polymerizing a specific perfluoroalkyl derivative and acrylate derivative monomer without cross-linking under specific conditions. The present inventors have further found that an oil-in-water emulsion cosmetic emulsified with the microparticle has excellent emulsion stability, less sticky feeling, and less powderiness or squeaky feeling.

Specifically, the core-corona polymer particle according to the present invention is obtained by radical-polymerizing a polyethylene oxide macromonomer represented by the following formula (1) and one or two or more of hydrophobic monomers represented by the following formulas (2) and (3) under the following conditions (A) to (D):

(A-1) the macromonomer represented by the following formula (1) is an acrylic acid derivative or a methacrylic acid derivative containing a polyethylene glycol group having 8 to 200 repeat units;

(A-2) the acrylate derivative monomer represented by the following formula (2) is an acrylic acid derivative or a methacrylic acid derivative having a substituent containing an alkyl group having 1 to 12 carbon atoms;
(A-3) the polyfluoroalkyl alcohol (meth)acrylic acid derivative monomer represented by the following formula (3) is an acrylic acid derivative or a methacrylic acid derivative having a substituent containing a perfluoroalkyl group having 1 to 12 carbon atoms;
(B) a molar ratio represented by molar quantity of the polyethylene oxide macromonomer added/molar quantity of (the hydrophobic monomer) added is 1:10 to 1:250;
(C) a polymerization solvent is a water-alcohol mixed solvent, and the alcohol is one or two or more members selected from ethanol, dipropylene glycol, 1,3-butylene glycol, and isoprene glycol; and
(D) solvent composition of the water-alcohol mixed solvent is water:alcohol=90 to 10:10 to 90 in terms of a mass ratio at 20° C.:

[Formula 1]

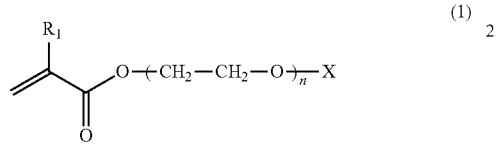

(1)

wherein $R_1$ represents hydrogen or methyl, X represents hydrogen or a hydrocarbon group having 1 to 3 carbon atoms, and n represents a number of 8 to 200;

[Formula 2]

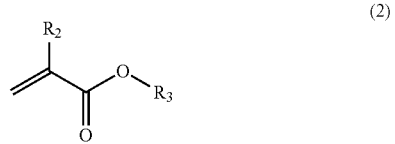

(2)

wherein $R_2$ represents hydrogen or a hydrocarbon group having 1 to 3 carbon atoms, and $R_3$ represents a hydrocarbon group having 1 to 12 carbon atoms;

[Formula 3]

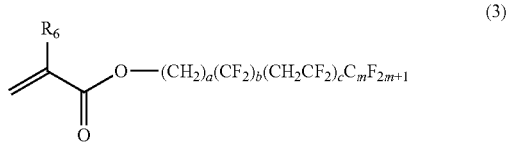

(3)

wherein a represents a number of 1 to 4, b represents a number of 1 to 12, c represents a number of 1 to 12, and m represents 1.
$R_6$ represents hydrogen or a hydrocarbon group having 1 to 3 carbon atoms.

The core-corona polymer particle is preferably used as a raw material for a cosmetic.
The core-corona polymer particle is preferably used as an emulsifier.

The core-corona polymer particle is preferably used as a clouding agent.

A particle size of the core-corona polymer particle is preferably 50 to 600 nm.

Effect of the Invention

According to the present invention, it has been found that a core-corona polymer particle that can be generally used in an oil-in-water emulsion cosmetic is obtained by radical-polymerizing a specific perfluoroalkyl derivative and acrylate derivative monomer without cross-linking under specific conditions. It has further been found that an oil-in-water emulsion cosmetic emulsified with the polymer particle has excellent emulsion stability, less sticky feeling, and less powderiness or squeaky feeling.

BRIEF DESCRIPTION OF THE DRAWING

FIG. 1 is a schematic view showing a microgel formation mechanism of the core-corona polymer particle of the present invention.

BEST MODE FOR CARRYING OUT THE INVENTION

The core-corona polymer particle according to the present invention is obtained by radical-polymerizing a polyethylene oxide macromonomer represented by the formula (1) given below and one or two or more of hydrophobic monomers represented by the formulas (2) and (3) given below under conditions (A) to (D) given below.

The polyethylene oxide macromonomer used in the present invention is represented by the following formula (1):

[Formula 1]

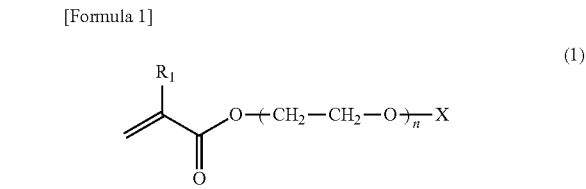

(1)

In the chemical formula (1), $R_1$ represents hydrogen or methyl, X represents hydrogen or a methyl group, and n represents a number of 8 to 200.

<Condition A1>

Condition A1 is that the polyethylene oxide macromonomer represented by the formula (1) is an acrylic acid derivative or a methacrylic acid derivative containing a polyethylene glycol group having 8 to 200 repeat units.

The polyethylene oxide macromonomer used in the present invention can be a commercially available product. Examples thereof include commercially available products manufactured by Sigma-Aldrich Co. LLC, and Blemmer® manufactured by NOF Corp.

The hydrophobic monomer used in the present invention can be preferably an acrylate derivative monomer represented by the formula (2) given below and the polyfluoroalkyl alcohol (meth)acrylic acid derivative monomer represented by the following formula (3)

The acrylate derivative monomer used in the present invention is represented by the following formula (2):

[Formula 2]

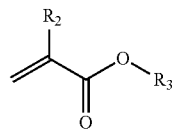

(2)

In the formula (2), $R_2$ represents hydrogen or a hydrocarbon group having 1 to 3 carbon atoms. $R_3$ represents a hydrocarbon group having 1 to 12 carbon atoms.

<Condition A2>

Condition A2 is that the acrylate derivative monomer represented by the formula (2) is an acrylic acid derivative or a methacrylic acid derivative having a substituent containing an alkyl group having 1 to 12 carbon atoms.

The acrylate derivative monomer used in the present invention can be a commercially available product from Sigma-Aldrich Co. LLC or Tokyo Chemical Industry Co., Ltd. for example can be used.

The polyfluoroalkyl alcohol (meth)acrylic acid derivative monomer used in the present invention is represented by the following formula (3):

[Formula 3]

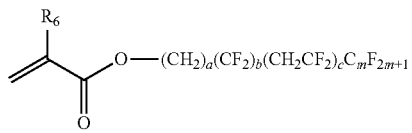

(3)

In the formula (3), a represents a number of 1 to 4, b represents a number of 1 to 12, c represents a number of 1 to 12, and m represents 1.

$R_6$ represents hydrogen or a hydrocarbon group having 1 to 3 carbon atoms.

<Condition A3>

Condition A3 is that the polyfluoroalkyl alcohol (meth) acrylic acid derivative monomer of the formula (3) is an acrylic acid derivative or a methacrylic acid derivative having a substituent containing a perfluoroalkyl group having 1 to 12 carbon atoms.

The polyfluoroalkyl alcohol (meth)acrylic acid derivative monomer used in the present invention can be a commercially available product. Examples thereof include products manufactured by Fluorochem Ltd.

<Condition B>

Condition B is that a molar ratio represented by molar quantity of the polyethylene oxide macromonomer added/ molar quantity of (the hydrophobic monomer) added is 1:10 to 1:250. If the molar ratio is less than 1:10, no core-corona particle may be formed because the polymer becomes hydrophilic. If the molar ratio exceeds 1:250, particles may be aggregated and precipitated because the polymer becomes hydrophobic.

<Condition C>

Condition C is that a polymerization solvent is a water-alcohol mixed solvent, and the alcohol is one or two or more members selected from ethanol, dipropylene glycol, 1,3-butylene glycol, and isoprene glycol.

<Condition D>

Condition D is that solvent composition of the water-alcohol mixed solvent is water:alcohol=90 to 10:10 to 90 in terms of a mass ratio at 20° C. Water:alcohol=50 to 10:90 to 50 is more preferred.

The core-corona polymer particle according to the present invention is preferably 0.01 to 10% by mass, more preferably 0.05 to 5% by mass, still more preferably 0.05 to 2% by mass, based on the pure content of the core-corona polymer particle with respect to the total amount of a cosmetic. If the amount of the core-corona polymer particle blended is less than 0.01% by mass, a stable cosmetic may not be obtained. If the amount of the core-corona polymer particle blended exceeds 10% by mass, stability may be poor in long-term preservation under high-temperature conditions or feeling of use may be poor.

The particle size of the core-corona polymer particle according to the present invention is preferably 50 to 600 nm. If the particle size is less than 50 nm, cloudiness may be markedly reduced. If the particle size exceeds 600 nm, particles may be precipitated or a function as an emulsifier may be deactivated.

As for the core-corona polymer particle according to the present invention, the present inventor has presumed that hydrophilic macromonomers and hydrophobic monomers are ordered, as shown in FIG. 1, in a solvent to form a core-corona polymer particle dispersion having an almost constant particle size and containing a cross-linked core moiety.

However, it has so far been impossible or substantially impractically difficult to completely identify the presence of this core-corona polymer particle in the state as shown in FIG. 1. Thus, it has been impossible to identify the invention of a product related to the present invention as the configuration of the product itself. Accordingly, this product-by-process invention is clear.

The core-corona polymer particle according to the present invention can be used in various cosmetic emulsifiers, clouding agents, raw materials for cosmetics, and the like.

(Oil-in-Water Emulsion Cosmetic)

The core-corona polymer particle of the present invention emulsifies an oil phase component and a water phase component to form an oil-in-water emulsion cosmetic having a structure where the core-corona microgel emulsifier is adsorbed on oil droplets of the oil phase component dispersed in the water phase component. Thus, the core-corona polymer particle of the present invention is excellent in emulsifying power. Furthermore, use of the raw material for a cosmetic of the present invention as an emulsifier can produce an oil-in-water emulsion cosmetic excellent in emulsion stability.

The oil-in-water emulsion cosmetic of the present invention is produced by mixing and dispersing the raw material for a cosmetic in water or a water phase component, and adding thereto an oil phase component and other components according to a routine method, followed by emulsification by stirring and application of shear force.

[Other Components]

The cosmetic comprising the cosmetic raw material according to the present invention can be produced according to a routine method depending on the dosage form of interest by appropriately blending, if necessary, other components, for example, an inorganic powder, an organic powder, an ester, an anionic surfactant, a cationic surfactant, an amphoteric surfactant, a nonionic surfactant, a moisturizing agent, a water-soluble polymer, a thickener, a film-forming agent, an ultraviolet absorber, a sequestering agent, a lower alcohol, a polyhydric alcohol, a sugar, an amino acid, an organic amine, a polymer emulsion, a pH adjuster, a skin nutrient, a vitamin, an antioxidant, an antioxidative aid, a fragrance, and water, without impairing the effect of the present invention.

Examples of the inorganic powder include talc, boron nitride, sericite, natural mica, calcined mica, synthetic mica, synthetic sericite, alumina, mica, kaolin, bentonite, smectite, calcium carbonate, magnesium carbonate, calcium phosphate, silicic anhydride, magnesium oxide, tin oxide, iron oxide, yttrium oxide, chromium oxide, zinc oxide, cerium oxide, aluminum oxide, magnesium oxide, chromium hydroxide, iron blue, ultramarine, calcium phosphate, aluminum hydroxide, barium sulfate, magnesium sulfate, silicic acid, aluminum magnesium silicate, calcium silicate, barium silicate, magnesium silicate, aluminum silicate, strontium silicate, silicon carbide, magnesium fluoride, tungstic acid metal salts, magnesium aluminate, magnesium aluminometasilicate, chlorohydroxyaluminum, clay, zeolite, hydroxyapatite, ceramic powders, spinel, mullite, cordierite, aluminum nitride, titanium nitride, silicon nitride, lanthanum, samarium, tantalum, terbium, europium, neodymium, Mn—Zn ferrite, Ni—Zn ferrite, silicone carbide, cobalt titanate, barium titanate, iron titanate, lithium cobalt titanate, cobalt aluminate, antimony-containing tin oxide, tin-containing indium oxide, magnetite, aluminum powders, gold powders, sliver powders, platinum powders, copper powders, noble metal colloids, iron powders, zinc powders, cobalt blue, cobalt violet, cobalt green, low-order titanium oxide, fine titanium oxide particles, butterfly-shaped barium sulfate, flower-shaped zinc oxide, tetrapod-shaped zinc oxide, fine zinc oxide particles, and pearl pigments such as titanium oxide-coated mica, titanium oxide-coated synthetic mica, titanium oxide-coated silica, titanium oxide-coated talc, zinc oxide-coated silica, titanium oxide-coated colored mica, red iron-coated titanated mica, red/black iron oxide-coated titanated mica, carmine-coated titanated mica, and iron blue-coated titanated mica.

Examples of the organic powder include (e.g., silicone elastomer powders, silicone powders, silicone resin-coated silicone elastomer powders, polyamide resin powders (nylon powders), polyethylene powders, polymethyl methacrylate powders (e.g., methyl methacrylate crosspolymers), polystyrene powders, styrene-acrylic acid copolymer resin powders, benzoguanamine resin powders, polytetrafluoroethylene powders, and cellulose powders); and organic pigments such as zirconium, barium and aluminum lake (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404.

Examples of the anionic surfactant include fatty acid soaps (e.g., sodium laurate and sodium palmitate); higher alkyl sulfuric acid ester salts (e.g., sodium lauryl sulfate and potassium lauryl sulfate); alkyl ether sulfuric acid ester salts (e.g., POE-triethanolamine lauryl sulfate and POE-sodium lauryl sulfate); N-acyl sarcosinates (e.g., lauroyl sarcosine sodium); higher fatty acid amide sulfonates (e.g., N-myristoyl-N-methyl taurine sodium, coconut oil fatty acid methyl taurid sodium, and methyl lauroyl taurate sodium); phosphoric acid ester salts (sodium POE-oleyl ether phosphate and POE-stearyl ether phosphoric acid); sulfosuccinates (e.g., sodium di-2-ethylhexylsulfosuccinate, sodium monolauroyl monoethanolamide polyoxyethylene sulfosuccinate, and sodium lauryl polypropylene glycol sulfosuccinate); alkylbenzenesulfonates (e.g., sodium linear dodecylbenzenesulfonate, triethanolamine linear dodecylbenzenesulfonate, and linear dodecylbenzenesulfonic acid); higher fatty acid ester sulfuric acid ester salts (e.g., sodium hydrogenated coconut oil fatty acid glycerin sulfate); N-acylglutamates (e.g., monosodium N-lauroyl glutamate, disodium N-stearoyl glutamate, and monosodium N-myristoyl-L-glutamate); sulfated oils (e.g., Turkey red oil); POE-alkyl ether carboxylic acids; POE-alkyl allyl ether carboxylates; α-olefin sulfonates; higher fatty acid ester sulfonates; secondary alcohol sulfuric acid ester salts; higher fatty acid alkylolamide sulfuric acid ester salts; sodium lauroyl monoethanolamide succinate; ditriethanolamine N-palmitoyl aspartate; and casein sodium.

Examples of the cationic surfactant include alkyl trimethyl ammonium salts (e.g., stearyl trimethyl ammonium chloride and lauryl trimethyl ammonium chloride); alkylpyridinium salts (e.g., cetylpyridinium chloride); distearyl dimethyl ammonium chloride dialkyl dimethyl ammonium salts; poly(N,N'-dimethyl-3,5-methylene piperidinium) chloride; alkyl quaternary ammonium salts; alkyl dimethyl benzyl ammonium salts; alkyl isoquinolinium salts; dialkyl morpholinium salts; POE-alkylamines; alkylamine salts; polyamine fatty acid derivatives; amyl alcohol fatty acid derivatives; benzalkonium chloride; and benzethonium chloride.

Examples of the amphoteric surfactant include imidazoline amphoteric surfactants (e.g., 2-undecyl-N,N,N-(hydroxyethylcarboxymethyl)-2-imidazoline sodium and 2-cocoyl-2-imidazolinium hydroxide-1-carboxyethyloxy disodium salt); and betaine surfactants (e.g., 2-heptadecyl-N-carboxymethyl-N-hydroxyethyl imidazolinium betaine, betaine lauryl dimethylaminoacetate, alkyl betaine, amide betaine, and sulfobetaine).

Examples of the lipophilic nonionic surfactant include sorbitan fatty acid esters (e.g., sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerin polyglycerin fatty acids (e.g., mono-cottonseed oil fatty acid glycerin, glycerin monoerucate, glycerin sesquioleate, glycerin monostearate, pyroglutamic acid glycerin α,α'-oleate, and malic acid glycerin monostearate); propylene glycol fatty acid esters (e.g., propylene glycol monostearate); hydrogenated castor oil derivatives; and glycerin alkyl ethers.

Examples of the hydrophilic nonionic surfactant include POE-sorbitan fatty acid esters (e.g., POE-sorbitan monooleate, POE-sorbitan monostearate, POE-sorbitan monooleate, and POE-sorbitan tetraoleate); POE-sorbitol fatty acid esters (e.g., POE-sorbitol monolaurate, POE-sorbitol monooleate, POE-sorbitol pentaoleate, and POE-sorbitol monostearate); POE-glycerin fatty acid esters (e.g., POE-monooleates such as POE-glycerin monostearate, POE-glycerin monoisostearate, and POE-glycerin triisostearate); POE-fatty acid esters (e.g., POE-distearate, POE-monodioleate, and ethylene glycol distearate); POE-alkyl ethers (e.g., POE-lauryl ether, POE-oleyl ether, POE-stearyl ether, POE-behenyl ether, POE-2-octyl dodecyl ether, and POE-cholestanol ether); Pluronic surfactants (e.g., Pluronic); POE.POP-alkyl ethers (e.g., POE.POP-cetyl ether, POE.POP-2-decyl tetradecyl ether, POE.POP-monobutyl ether, POE.POP-hydrogenated lanoline, and POE.POP-glycerin ether); tetra-POE/tetra-POP-ethylenediamine condensates (e.g., Tetronic); POE-castor oil hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamic acid monoisostearic acid diester, and POE-hydrogenated castor oil maleic acid); POE-beeswax/lanoline derivatives (e.g., POE-sorbitol beeswax); alkanolamides (e.g., coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkyl ethoxy dimethylamine oxides; and trioleyl phosphoric acid.

Examples of the moisturizing agent include polyethylene glycol, propylene glycol, glycerin, 1,3-butylene glycol, xylitol, sorbitol, maltitol, chondroitin sulfate, hyaluronic acid, mucoitin sulfate, caronic acid, atelocollagen, cholesteryl-12-hydroxystearate, sodium lactate, bile acid salt, dl-pyrrolidone carboxylate, alkylene oxide derivatives, short-chain soluble collagen, diglycerin (EO) PO adducts, *Rosa roxburghii* fruit extracts, *Achillea millefolium* extracts, and melilot extracts.

Examples of the natural water-soluble polymer include plant-derived polymers (e.g., gum arabic, tragacanth gum, galactan, guar gum, carob gum, karaya gum, carrageenan, pectin, agar, quince seeds (marmelo), algae colloids (*Fucus vesiculosus* extracts), starch (rice, corn, potato, and wheat starches), and glycyrrhizic acid); microorganism-derived polymers (e.g., xanthan gum, dextran, succinoglucan, and pullulan); and animal-derived polymers (e.g., collagen, casein, albumin, and gelatin).

Examples of the semisynthetic water-soluble polymer include starch polymers (e.g., carboxymethyl starch and methylhydroxypropyl starch); cellulose polymers (methylcellulose, ethylcellulose, methylhydroxypropylcellulose, hydroxyethylcellulose, cellulose sodium sulfate, hydroxypropylcellulose, carboxymethylcellulose, carboxymethylcellulose sodium, crystalline cellulose, cellulose powders, etc.); and alginic acid polymers (e.g., sodium alginate and alginic acid propylene glycol ester).

Examples of the synthetic water-soluble polymer include vinyl polymers (e.g., polyvinyl alcohol, polyvinyl methyl ether, polyvinylpyrrolidone, and carboxyvinyl polymers); polyoxyethylene polymers (e.g., polyoxyethylene-polyoxypropylene copolymers of polyethylene glycol 20,000, 40,000, or 60,0000); acrylic polymers (e.g., sodium polyacrylate, polyethyl acrylate, and polyacrylamide); polyethyleneimine; and cationic polymers.

Examples of the thickener include gum arabic, carrageenan, karaya gum, tragacanth gum, carob gum, quince seeds (marmelo), casein, dextrin, gelatin, sodium pectinate, sodium alginate, methylcellulose, ethylcellulose, CMC, hydroxyethylcellulose, hydroxypropylcellulose, PVA, PVM, PVP, sodium polyacrylate, carboxyvinyl polymers, locust bean gum, guar gum, tamarind gum, cellulose dialkyl dimethyl ammonium sulfate, xanthan gum, aluminum magnesium silicate, bentonite, hectorite, AlMg silicate (Veegum), laponite, and silicic anhydride.

Examples of the ultraviolet absorber include benzoic acid ultraviolet absorbers (e.g., p-aminobenzoic acid (hereinafter, abbreviated to PABA), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester); anthranilic acid ultraviolet absorbers (e.g., homomenthyl-N-acetyl anthranilate); salicylic acid ultraviolet absorbers (e.g., amyl salicylate, menthyl salicylate, homomenthyl salicylate, octyl salicylate, phenyl salicylate, benzyl salicylate, and p-isopropanolphenyl salicylate); cinnamic acid ultraviolet absorbers (e.g., octylmethoxy cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate, and glyceryl mono-2-ethylhexanoyl-di-p-methoxy cinnamate); benzophenone ultraviolet absorbers (e.g., 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, and 4-hydroxy-3-carboxybenzophenone); 3-(4'-methylbenzylidene)-d,l-camphor and 3-benzylidene-d,l-camphor; 2-phenyl-5-methylbenzoxazole; 2,2'-hydroxy-5-methylphenylbenzotriazole; 2-(2'-hydroxy-5'-t-octylphenyl) benzotriazole; 2-(2'-hydroxy-5'-methylphenylbenzotriazole; dibenzalazine; dianisoylmethane; 4-methoxy-4'-t-butyldibenzoylmethane; 5-(3,3-dimethyl-2-norbornylidene)-3-pentan-2-one and dimorpholinopyridazino; 2-ethylhexyl-2-cyano-3,3-diphenyl acrylate; and 2,4-bis-{[4-(2-ethylhexyloxy)-2-hydroxy]-phenyl}-6-(4-methoxyphenyl)-(1,3,5)-triazine.

Examples of the sequestering agent include 1-hydroxyethane-1,1-diphosphonic acid, 1-hydroxyethane-1,1-diphosphonic acid tetrasodium salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, and trisodium ethylenediamine hydroxyethyl triacetate.

Examples of the lower alcohol include ethanol, propanol, isopropanol, isobutyl alcohol, and t-butyl alcohol.

Examples of the polyhydric alcohol include dihydric alcohols (e.g., ethylene glycol, propylene glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, and octylene glycol); trihydric alcohols (e.g., glycerin and trimethylolpropane); tetrahydric alcohols (e.g., pentaerythritol such as 1,2,6-hexanetriol); pentahydric alcohols (e.g., xylitol); hexahydric alcohols (e.g., sorbitol and mannitol); polyhydric alcohol polymers (e.g., diethylene glycol, dipropylene glycol, triethylene glycol, polypropylene glycol, tetraethylene glycol, diglycerin, polyethylene glycol, triglycerin, tetraglycerin, and polyglycerin); dihydric alcohol alkyl ethers (e.g., ethylene glycol monomethyl ether, ethylene glycol monoethyl ether, ethylene glycol monobutyl ether, ethylene glycol monophenyl ether, ethylene glycol monohexyl ether, ethylene glycol mono-2-methylhexyl ether, ethylene glycol isoamyl ether, ethylene glycol benzyl ether, ethylene glycol isopropyl ether, ethylene glycol dimethyl ether, ethylene glycol diethyl ether, and ethylene glycol dibutyl ether); dihydric alcohol alkyl ethers (e.g., diethylene glycol monomethyl ether, diethylene glycol monoethyl ether, diethylene glycol monobutyl ether, diethylene glycol dimethyl ether, diethylene glycol diethyl ether, diethylene glycol butyl ether, diethylene glycol methyl ethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, and dipropylene glycol butyl ether); dihydric alcohol ether esters (e.g., ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disuccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, and propylene glycol monophenyl ether acetate); glycerin monoalkyl ethers (e.g., xyl alcohol, selachyl alcohol, and batyl alcohol); sugar alcohols (e.g., sorbitol, maltitol, maltotriose, mannitol, sucrose, erythritol, glucose, fructose, sugars obtained by starch decomposition, maltose, xylitose, and reduced alcohols of sugars obtained by starch decomposition); Glysolid; tetrahydrofurfuryl alcohol; POE-tetrahydrofurfuryl alcohol; POP-butyl ether; POP-.POE-butyl ether; tripolyoxypropylene glycerin ether; POP-glycerin ether; POP-glycerin ether phosphoric acid; and POP.POE-pentane erythritol ether and polyglycerin.

Examples of the monosaccharide include trioses (e.g., D-glyceryl aldehyde and dihydroxyacetone); tetroses (e.g., D-erythrose, D-erythrulose, D-threose, and erythritol); pentoses (e.g., L-arabinose, D-xylose, L-lyxose, D-arabinose, D-ribose, D-ribulose, D-xylulose, and L-xylulose); hexoses (e.g., D-glucose, D-talose, D-psicose, D-galactose, D-fructose, L-galactose, L-mannose, and D-tagatose); heptoses (e.g., aldoheptose and heplose); octoses (e.g., octulose); deoxy sugars (e.g., 2-deoxy-D-ribose, 6-deoxy-L-galactose, and 6-deoxy-L-mannose); amino sugars (e.g., D-glucosamine, D-galactosamine, sialic acid, aminouronic acid, and muramic acid); and uronic acids (e.g., D-glucuronic acid, D-mannuronic acid, L-gluronic acid, D-galacturonic acid, and L-iduronic acid).

Examples of the oligosaccharide include sucrose, gentianose, umbelliferose, lactose, planteose, isolychnoses, α,α-trehalose, raffinose, lychnoses, umbilicin, stachyose verbascoses.

Examples of the polysaccharide include cellulose, quince seeds, chondroitin sulfate, starch, galactan, dermatan sulfate, glycogen, gum arabic, heparan sulfate, hyaluronic acid, tragacanth gum, keratan sulfate, chondroitin, xanthan gum, mucoitin sulfate, guar gum, dextran, keratosulfate, locust bean gum, succinoglucan, and charonin.

Examples of the amino acid include neutral amino acids (e.g., threonine and cysteine); and basic amino acids (e.g., hydroxylysine). Examples of the amino acid derivative include acyl sarcosine sodium (lauroyl sarcosine sodium), acylglutamate, acyl β-alanine sodium, glutathione, and pyrrolidonecarboxylic acid.

Examples of the organic amine include monoethanolamine, diethanolamine, triethanolamine, morpholine, triisopropanolamine, 2-amino-2-methyl-1,3-propanediol, and 2-amino-2-methyl-1-propanol.

Examples of the polymer emulsion include acrylic resin emulsions, polyethyl acrylate emulsions, acrylic resin fluids, polyacrylic alkyl ester emulsions, polyvinyl acetate resin emulsions, and natural rubber latex.

Examples of the pH adjuster include buffers such as lactic acid-sodium lactate, citric acid-sodium citrate, and succinic acid-sodium succinate.

Examples of the vitamins include vitamins A, B1, B2, B6, C, E and derivatives thereof, pantothenic acid and derivatives thereof, and biotin.

Examples of the antioxidant include tocopherols, dibutylhydroxytoluene, butylhydroxyanisole, and gallic acid esters.

Examples of the antioxidative aid include phosphoric acid, citric acid, ascorbic acid, maleic acid, malonic acid, succinic acid, fumaric acid, kephalin, hexametaphosphate, phytic acid, and ethylenediaminetetraacetic acid.

Examples of other components that may be blended include antiseptics (ethylparaben, butylparaben, chlorphenesin, phenoxyethanol, etc.); antiphlogistics (e.g., glycyrrhizic acid derivatives, glycyrrhetinic acid derivatives, salicylic acid derivatives, hinokitiol, zinc oxide, and allantoin); skin-lightening agents (e.g., placenta extracts, *Saxifraga stolonifera* extracts, and arbutin); various extracts (e.g., phellodendron bark, coptis rhizome, lithospermum root, *Paeonia lactiflora*, swertia herb, birch, sage, loquat, carrot, aloe, mallow, iris, grape, coix seed, luffa, lily, saffron, cnidium rhizome, ginger, hypericum, Ononis, garlic, capsicum, citrus unshiu peel, *Japanese angelica* root, and algae), activators (e.g., royal jelly, photosensitizers, and cholesterol derivatives); blood flow stimulants (e.g., nonanoic acid vanillylamide, nicotinic acid benzyl ester, nicotinic acid β-butoxy ethyl ester, capsaicin, zingerone, cantharides tincture, ichthammol, tannic acid, α-borneol, tocopherol nicotinate, inositol hexanicotinate, cyclandelate, cinnarizine, tolazoline, acetylcholine, verapamil, cepharanthine, and γ-oryzanol); anti-seborrheic agents (e.g., sulfur and thianthol); and anti-inflammatory agents (e.g., tranexamic acid, thiotaurine, and hypotaurine).

Further, for example, sequestering agents such as disodium edetate, trisodium edetate, sodium citrate, sodium polyphosphate, sodium metaphosphate, gluconic acid, and malic acid, various crude drug extracts such as caffein, tannin, verapamil, tranexamic acid and derivatives thereof, licorice, Chinese quince, and *Pyrola japonica*, chemicals such as tocopherol acetate, glycyrrhetinic acid, glycyrrhizic acid and derivatives thereof and salts thereof, skin lightening agents such as vitamin C, magnesium ascorbyl phosphate, glucoside ascorbate, arbutin, and kojic acid, amino acids such as arginine and lysine and derivatives thereof, and sugars such as fructose, mannose, erythritol, trehalose, and xylitol can be appropriately blended.

The product form of the raw material for a cosmetic, comprising the core-corona polymer particle according to the present invention can adopt every product form. Specifically, product forms such as lotions, milky lotions, beauty essences, creams, sunscreens, and liquid foundations can be adopted.

[Method for Producing Core-Corona Polymer Particle]

The core-corona polymer particle can be produced by a method known in the art. The method is, for example, as follows: to a three-neck flask equipped with a reflux tube and a nitrogen feed tube, a predetermined solvent (e.g., a water-alcohol mixed solvent) is added, and a polyethylene oxide monomer and hydrophobic monomers are added. After sufficient dissolution or dispersion, the flask is purged with nitrogen for 20 minutes or longer to remove dissolved oxygen. Then, 1% by mol of a radical polymerization initiator with respect to the total amount of the monomers is added and dissolved. The polymerization solution with homogeneous dissolution or dispersion is purged with nitrogen to remove dissolved oxygen. Then, polymerization reaction is performed for 8 hours at a temperature kept at 65 to 70° C. in an oil bath with stirring. After the completion of polymerization, a core-corona polymer particle dispersion is obtained.

[Method for Producing Cosmetic Comprising Core-Corona Polymer Particle According to Present Invention]

The cosmetic can be produced by a method known in the art. Examples thereof include a method of adding a predetermined solubilizer and oil into water containing the core-corona polymer particle to obtain a solubilized lotion, and a method of adding an oil into water containing the core-corona polymer particle and a water-soluble thickener, and then applying strong shear force thereto using a homomixer to obtain a milky lotion.

EXAMPLES

Hereinafter, the present invention will be described in more detail with reference to Examples. However, the present invention is not limited thereby. The amounts of components blended are indicated by % by mass with respect to the system into which the components are to be blended, unless otherwise specified.

Methods for evaluating the core-corona polymer particle according to the present invention will be described prior to the description of Examples.

Evaluation (1): Evaluation of Transmittance

A sample was measured at a wavelength of 600 nm using a spectrophotometer V-630 (manufactured by JASCO Corp.) and evaluated for its visible light transmittance (light path: 1 cm). Ion-exchanged water was used as a reference.

Evaluation (2-1): Evaluation of Stability (Appearance)

The appearance of a sample was visually observed 1 day after its preparation and evaluated according to the following criteria.

(Evaluation Criteria)
A: The sample was homogeneous without oil floating and/or powder aggregation.
B: The sample was almost homogeneous, though oil floating and/or powder aggregation was slightly observed.
C: The sample was not homogeneous, or marked separation of the oil phase or powder aggregation was observed.

Evaluation (2-2): Evaluation of Emulsion Stability (Emulsified Particle)

Emulsified particles of a sample were observed under an optical microscope.

(Evaluation Criteria)
A: The emulsified particles were homogeneous and were neither unified nor aggregated.
B: The emulsified particles were almost homogeneous, though slight unification, aggregation, or the like was observed.
C: The emulsified particles were not homogeneous, and marked unification and/or aggregation were observed.

Evaluation (3): Evaluation of Skin Irritation Test

An occluded patch was applied for 24 hours to the inner side of the upper arms of 10 panelists having sensitive skin. The state of the skin was determined according to the following criteria.

(Evaluation Criteria)
0 . . . No abnormality was observed.
1 . . . Slight redness was observed.
2 . . . Redness was observed.
3 . . . Redness and papula were observed.

Evaluation (4): Evaluation of Feeling of Use

Ten specialized panelists evaluated feeling of use ("absence of stickiness", "rich feeling", and "rapidity of spreading") upon application of a sample to the skin according to the following criteria.

(Evaluation Criteria)
A: 7 or more out of the 10 panelists answered "good" or "actually felt".
B: 5 or more out of the 10 panelists answered "good" or "actually felt".
C: 3 or more out of the 10 panelists answered "good" or "actually felt".
D: 2 or less out of the 10 panelists answered "good" or "actually felt".

Evaluation (5): Evaluation of Time-Dependent Stability

The state of an oil-in-water emulsion cosmetic was visually observed after a lapse of 1 month from production.

(Evaluation Criteria)
A: The sample maintained an emulsion state obtained at the time of production.
B: The sample almost maintained an emulsion state, though slight precipitation and/or floating was seen.
C: Emulsified particles were precipitated and/or floated, and particles were also unified.
D: Emulsified particles in the sample were precipitated and/or floated and unified so that the oil phase was completely separated.

[Raw Material for Cosmetic Containing Dispersed Core-Corona Polymer Particle]

First, the present inventors produced and evaluated the core-corona polymer particle according to the present invention by the evaluation methods. The amount of each component blended is described in Table 1. Conditions for radical-polymerizing components are described in Table 2. Each evaluation of the obtained core-corona polymer particle dispersed in the raw material for a cosmetic is described in Table 3.

TABLE 1

| | Macromonomer Methoxy | Hydrophobic monomer | | | Polymerization solvent | |
| | | Methyl | n-Butyl | 1H;1H;2H;2H-Perfluoro octyl | | |
| | PEG4000 | methacrylate | methacrylate | methacrylate | | Alcohol | Amount of |
| Production Example 1 | Formula (1) | Formula (2) | Formula (2) | Formula (3) | Water | species | alcohol |
| Amount blended | 4.17 | 1.76 | 2.50 | 1.57 | 36 | EtOH | 54 |

TABLE 2

Conditions of Production Example 1

| (A1) Macromonomer Formula (1) | (A2) Acrylate derivative monomer Formula (2) | (A3) Polyfluoroalkyl monomer | (B) Macromonomer/ Hydrophobic monomer ratio (molar ratio) | (C) Alcohol species | (D) Water/ Alcohol solvent mixing ratio |
|---|---|---|---|---|---|
| $R_1 = CH_3$<br>n = 90 | $R_2 = CH_3$<br>$R_3 = CH_3$ | $R_2 = CH_3$<br>$R_3 = nC_4H_9$ | $R_6 = CH_3$<br>a = 2, b = 5,<br>c = 0, m = 1 | 1/50 | EtOH | 40/60 |

TABLE 3

Production Example 1

| Appearance | Particle size (nm) | Degree of dispersion |
|---|---|---|
| Cloudy solution-like | 123.1 | 0.095 |

The raw material for a cosmetic obtained in Production Example 1 contained dispersed core-corona polymer particles.

Next, the core-corona polymer particles obtained in Production Example 1 were used in a cloudy cosmetic.

TABLE 4

| | Test Example 1-1 |
|---|---|
| Ion-exchanged water | Balance |
| Core-corona particle of Test Example 1 | 1 |
| Ethanol | 0.54 |
| Dipropylene glycol | — |
| 1,3-Butylene glycol | 1 |
| Glycerin | 3 |
| Polyethylene glycol 1000 | 0.5 |
| Peony extract | 0.01 |
| Raspberry extract | 0.01 |
| *Saxifraga stolonifera* extracts | 0.01 |
| Menthol | 0.02 |
| Citric acid (food) | 0.02 |
| Sodium citrate | 0.08 |
| Sodium hexametaphosphate | 0.03 |
| Phenoxyethanol | 0.3 |
| Fragrance | 0.05 |
| Evaluation (1): 600 nm transmittance (%) | 73.2 |
| Evaluation (2-1): stability | A |
| Evaluation (3): skin irritancy | 0 |
| Evaluation (4-1): absence of stickiness | A |
| Evaluation (4-2): rich feeling | B |
| Evaluation (4-3): rapidity of spreading | B |

The obtained cloudy cosmetic was excellent in terms of stability, skin irritancy, and feeling of use.

Next, an oil-in-water emulsion cosmetic was produced using the core-corona polymer particles obtained in Production Example 1.

TABLE 5

| | Test Example 2-1 |
|---|---|
| Ion-exchanged water | Balance |
| Core-corona particle of Production Example 1 | 1 |
| Ethanol | 5.4 |
| Dipropylene glycol | — |
| 1,3-Butylene glycol | 3 |
| Liquid paraffin | 10 |
| Glycerin tri-2-ethylhexanoate | 10 |
| Dimethylpolysiloxane (6 cs) | 10 |
| Carboxyvinyl polymer | 0.1 |
| Potassium hydroxide | 0.06 |
| Phenoxyethanol | 0.3 |
| Chelating agent | q.s. |
| Fragrance | q.s. |
| Evaluation (2-1): emulsion stability (appearance) | A |
| Evaluation (2-2): emulsion stability (particle) | A |
| Evaluation (3): skin irritancy | 0 |
| Evaluation (4-1): wateriness | A |
| Evaluation (4-2): absence of squeaky feeling | A |
| Evaluation (4-3): absence of powderiness | A |
| Evaluation (5): time-dependent stability | B |

TABLE 6

| | Test Example 3-1 |
|---|---|
| Ion-exchanged water | Balance |
| Core-corona particle of Production Example 1 | 1 |
| Ethanol | 5.4 |
| Dipropylene glycol | — |
| 1,3-Butylene glycol | 3 |
| Liquid paraffin | 20 |
| Glycerin tri-2-ethylhexanoate | 20 |
| Dimethylpolysiloxane (6 cs) | 20 |
| Carboxyvinyl polymer | 0.05 |
| Potassium hydroxide | 0.03 |
| Phenoxyethanol | 0.3 |
| Chelating agent | q.s. |
| Fragrance | q.s. |
| Evaluation (2-1): emulsion stability (appearance) | A |
| Evaluation (2-2): emulsion stability (particle) | A |
| Evaluation (3): skin irritancy | 0 |
| Evaluation (4-1): wateriness | A |
| Evaluation (4-2): absence of squeaky feeling | A |
| Evaluation (4-3): absence of powderiness | A |
| Evaluation (5): time-dependent stability | A |

TABLE 7

|  | Test Example 4-1 |
|---|---|
| Ion-exchanged water | Balance |
| Core-corona particle of Production Example 1 | 1 |
| Ethanol | 5.4 |
| Dipropylene glycol | — |
| Dimethylacrylamide/Sodium acryloyldimethyltaurate crosspolymer | 1 |
| Phenoxyethanol | 0.3 |
| Chelating agent | q.s. |
| Fragrance | q.s. |
| Evaluation (2-1): emulsion stability (appearance) | A |
| Evaluation (2-2): emulsion stability (particle) | A |
| Evaluation (3): skin irritancy | 0 |
| Evaluation (4-1): wateriness | A |
| Evaluation (4-2): absence of squeaky feeling | A |
| Evaluation (4-3): absence of powderiness | A |
| Evaluation (5): time-dependent stability | A |

The oil-in-water emulsion cosmetics obtained in Test Examples 2-1 to 4-1 were excellent in terms of stability, skin irritancy, and feeling of use.

What is claimed is:

1. A core-corona polymer particle obtained by radical-polymerizing a polyethylene oxide macromonomer represented by the following formula (1) and one or two or more of hydrophobic monomers represented by the following formula (3) and optionally one or two or more additional hydrophobic monomers represented by the following formula (2) under the following conditions:
   (A-1) the macromonomer represented by the following formula (1) is an acrylic acid derivative or a methacrylic acid derivative containing a polyethylene glycol group having 8 to 200 repeat units;
   (A-2) an acrylate derivative monomer represented by the following formula (2) is an acrylic acid derivative or a methacrylic acid derivative having a substituent containing an alkyl group having 1 to 12 carbon atoms;
   (A-3) a polyfluoroalkyl alcohol (meth)acrylic acid derivative monomer represented by the following formula (3) is an acrylic acid derivative or a methacrylic acid derivative having a substituent containing a perfluoroalkyl group having 1 to 12 carbon atoms;
   (B) a molar ratio represented by molar quantity of the polyethylene oxide macromonomer added/molar quantity of (the hydrophobic monomer) added is 1:10 to 1:250;
   (C) a polymerization solvent is a water-alcohol mixed solvent, and the alcohol is one or two or more members selected from ethanol, dipropylene glycol, 1,3-butylene glycol, and isoprene glycol; and
   (D) solvent composition of the water-alcohol mixed solvent is water:alcohol from 90:10 to 10:90 in terms of a mass ratio at 20° C.;
   wherein formula (1) is as follows:

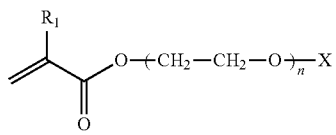

(1)

wherein $R_1$ represents hydrogen or methyl, X represents hydrogen or a hydrocarbon group having 1 to 3 carbon atoms, and n represents a number of 8 to 200;
wherein formula (2) is as follows:

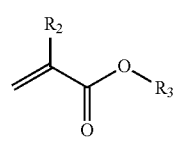

(2)

wherein $R_2$ represents hydrogen or a hydrocarbon group having 1 to 3 carbon atoms, and $R_3$ represents a hydrocarbon group having 1 to 12 carbon atoms;
wherein formula (3) is as follows:

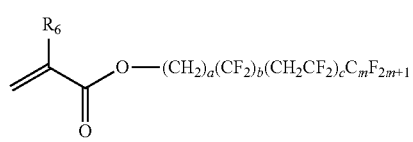

(3)

wherein a represents a number of 1 to 4, b represents a number of 1 to 12, c represents a number of 1 to 12, m represents 1, and
wherein $R_6$ represents hydrogen or a hydrocarbon group having 1 to 3 carbon atoms.

2. An emulsifier comprising a core-corona polymer particle according to claim 1.

3. A clouding agent comprising a core-corona polymer particle according to claim 1.

4. The core-corona polymer particle according to claim 1, wherein a particle size of the core-corona polymer particle is 50 to 600 nm.

5. A cosmetic raw material comprising a core-corona polymer particle according to claim 1.

* * * * *

UNITED STATES PATENT AND TRADEMARK OFFICE
CERTIFICATE OF CORRECTION

| | |
|---|---|
| PATENT NO. | : 11,596,583 B2 |
| APPLICATION NO. | : 16/982348 |
| DATED | : March 7, 2023 |
| INVENTOR(S) | : Sugiyama et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 235 days.

Signed and Sealed this
Tenth Day of September, 2024

Katherine Kelly Vidal
*Director of the United States Patent and Trademark Office*